United States Patent
Pearce et al.

(10) Patent No.: US 8,551,913 B2
(45) Date of Patent: Oct. 8, 2013

(54) METHODS AND COMPOSITIONS FOR REDUCING SEED BRIDGING

(75) Inventors: Jeremy D. Pearce, Bosham (GB); R. D. Piran Cargeeg, Saskatoon, CA (US)

(73) Assignee: Becker Underwood, Inc., Ames, IA (US)

( * ) Notice: Subject to any disclaimer, the term of this patent is extended or adjusted under 35 U.S.C. 154(b) by 0 days.

(21) Appl. No.: 13/370,424

(22) Filed: Feb. 10, 2012

(65) Prior Publication Data

US 2012/0208699 A1   Aug. 16, 2012

Related U.S. Application Data

(60) Provisional application No. 61/442,027, filed on Feb. 11, 2011.

(51) Int. Cl.
*A01N 25/26* (2006.01)
*A01N 25/00* (2006.01)

(52) U.S. Cl.
USPC ..................................... 504/100; 504/116.1

(58) Field of Classification Search
None
See application file for complete search history.

(56) References Cited

U.S. PATENT DOCUMENTS

| | | | |
|---|---|---|---|
| 5,292,507 A * | 3/1994 | Charley | 424/93.4 |
| 5,683,957 A | 11/1997 | Huang et al. | |
| 2002/0177526 A1 * | 11/2002 | Chen et al. | 504/100 |
| 2007/0074451 A1 * | 4/2007 | Pearce et al. | 47/57.6 |
| 2008/0132411 A1 * | 6/2008 | Watt et al. | 504/100 |
| 2011/0059846 A1 | 3/2011 | Gutsche et al. | |
| 2011/0257010 A1 | 10/2011 | Koltzenburg et al. | |

FOREIGN PATENT DOCUMENTS

| | | | |
|---|---|---|---|
| EP | 0 818 135 A1 | | 1/1998 |
| EP | 818 135 | * | 1/1998 |
| WO | WO 2004047516 | * | 6/2004 |
| WO | WO2004047516 A1 | | 10/2004 |
| WO | WO2005113470 A2 | | 12/2005 |
| WO | WO2010111309 A1 | | 9/2010 |

* cited by examiner

*Primary Examiner* — Alton Pryor
(74) *Attorney, Agent, or Firm* — Davis, Brown, Koehn, Shors & Roberts, P.C.; Sean D. Solberg

(57) ABSTRACT

The various embodiments disclosed herein relate to methods and compositions for reducing the bridging of treated seeds, including some that also enhance the survivability of any beneficial microorganisms included in the composition or mixed therewith and/or enhance the yield of the plants that grow from the seed to which the treatment is applied. The various compositions can include sugar and oil, while other embodiments include sugar, oil, and an emulsifying agent, and certain embodiments include sugar, oil, and at least one microorganism. In various embodiments, the oil can be, for example, a heavy lubricating oil such as mineral oil or silicone oil, and the sugar can be, for example, a non-reducing sugar.

16 Claims, 4 Drawing Sheets

METHODS AND COMPOSITIONS FOR REDUCING SEED BRIDGING

CROSS-REFERENCE TO RELATED APPLICATION(S)

This application claims priority from U.S. Provisional Application No. 61/442,027, filed Feb. 11, 2011, which is hereby incorporated by reference in its entirety.

FIELD OF THE INVENTION

The various embodiments disclosed or contemplated herein relate to methods and compositions for reducing seed bridging.

BACKGROUND OF THE INVENTION

"Seed bridging," as used herein, means the formation of solid masses of seeds that are adhered to each other or bound together as a result of a seed treatment that creates an adhesion or bond amongst seeds that come into contact with each other after the seed treatment is applied. Various seed treatments can cause such bridging as a result of the "stickiness" of the seeds that results from the treatment. The seed bridging results in a solid mass or clump of seeds that can prevent or significantly hinder the ability of the seeds to be moved out of various types of seed containers. When this seed bridging occurs, the only remedy is to break up the solid masses using some mechanical means.

There is a need in the art for improved methods and compositions that can reduce seed bridging.

BRIEF SUMMARY OF THE INVENTION

Discussed herein are various methods and compositions for reducing seed bridging. In addition, certain embodiments relate to enhancement of survivability of one or more beneficial microorganisms.

In Example 1, a seed treatment composition comprises a sugar, an oil, and an emulsifying agent, the composition reducing seed bridging of seeds treated with the composition.

Example 2 relates to the composition of Example 1, further comprising at least one microorganism.

Example 3 relates to the composition of Example 2, wherein the composition enhances the survivability of the at least one microorganism.

Example 4 relates to the composition of Example 2, wherein the composition enhances yield of plants growing from the seeds.

In Example 5, a seed treatment composition comprises a non-reducing sugar, an oil, and lecithin, the composition reducing seed bridging of seeds treated with the composition. The non-reducing sugar comprises sucrose or sorbitol. The oil comprises at least one of mineral oil or silicon oil.

Example 6 relates to the composition of Example 5, wherein the non-reducing sugar is present in an amount ranging from about 30% to about 70% w/v.

Example 7 relates to the composition of Example 5, wherein the oil is present in an amount ranging from about 5% to about 60% w/v.

Example 8 relates to the composition of Example 5, wherein the lecithin is present in an amount ranging from about 0.05% to about 6.0% w/v.

Example 9 relates to the composition of Example 5, further comprising at least one microorganism.

Example 10 relates to the composition of Example 9, wherein the at least one microorganism is *Rhizobium*.

Example 11 relates to the composition of Example 9, wherein the composition enhances the survivability of the at least one microorganism.

Example 12 relates to the composition of Example 9, wherein the composition enhances yield of plants growing from the seeds.

In Example 13, a seed treatment composition comprises at least one non-reducing sugar, at least one heavy lubricating oil, an emulsifying agent, and at least one microorganism, the composition reducing seed bridging of seeds treated with the composition, enhancing the viability of the at least one microorganism, and enhancing yield of plants growing from the seeds. The at least one non-reducing sugar is present in an amount ranging from about 30% to about 70% w/v. The at least one heavy lubricating oil is present in an amount ranging from about 5% to about 60% w/v. The emulsifying agent is present in an amount ranging from about 0.05% to about 2.0% w/v.

Example 14 relates to the composition of Example 13, further comprising at least one polymer component.

Example 15 relates to the composition of Example 13, further comprising a commercial extender composition.

Example 16 relates to the composition of Example 13, further comprising a commercial extender composition, wherein the at least one non-reducing sugar is a component of the commercial extender composition.

Example 17 relates to the composition of Example 13, further comprising a buffer component.

Example 18 relates to the composition of Example 13, further comprising a pesticide.

Example 19 relates to the composition of Example 13, wherein the at least one microorganism is a *Rhizobium*.

Example 20 relates to the composition of Example 13, further comprising a mixture of at least two microorganisms.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Various embodiments disclosed herein relate to compositions for reducing the bridging of treated seeds. Certain embodiments also relate to compositions that not only reduce bridging, but also enhance the survivability of any beneficial microorganisms included in the seed treatment and/or enhance the yield of the seed to which a treatment containing microorganisms is applied. The various composition implementations can include sugar and oil, while other embodiments include sugar, oil, and an emulsifying agent. In various embodiments, the oil can be, for example, a heavy lubricating oil such as mineral oil or silicone oil, and the sugar can be, for example, a non-reducing sugar.

For purposes of this application, "seed bridging" is defined as set forth above in the Background. As used herein, seed bridging and "flowability" are two different concepts. That is, flowability relates to the relative ability of seed that is already in a flowable state to flow. It is the degree to which the seed can flow. In contrast, seed bridging describes seed that is in a state in which it cannot flow. As such, there is not necessarily a direct relationship between seed bridging reduction and flowability. That is, a reduction in bridging of certain seed does not necessarily mean that the flowability of the same seed has been enhanced.

Figure 1A:
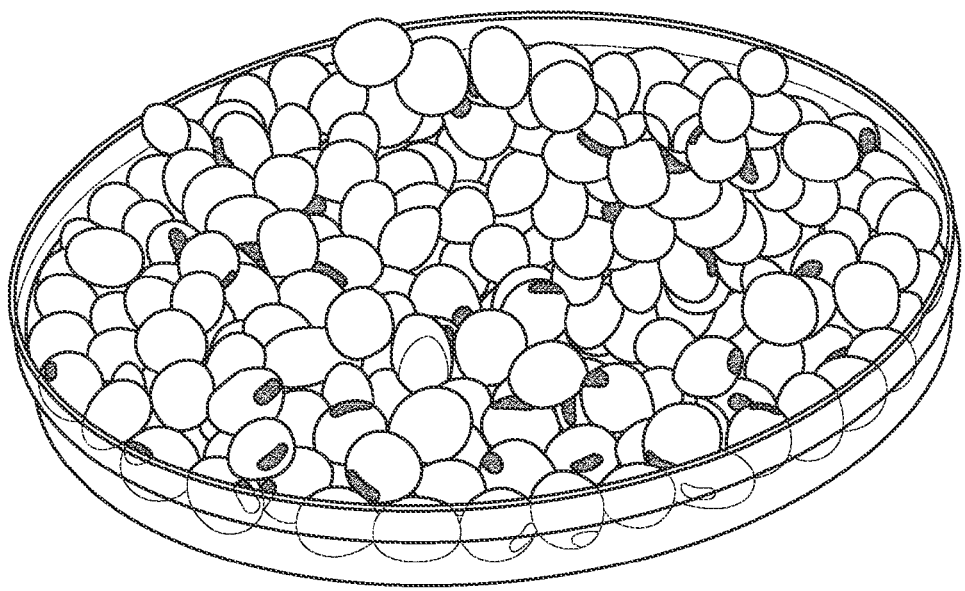
FIG. 1A depicts seed that is not exhibiting seed bridging.
Figure 1B:
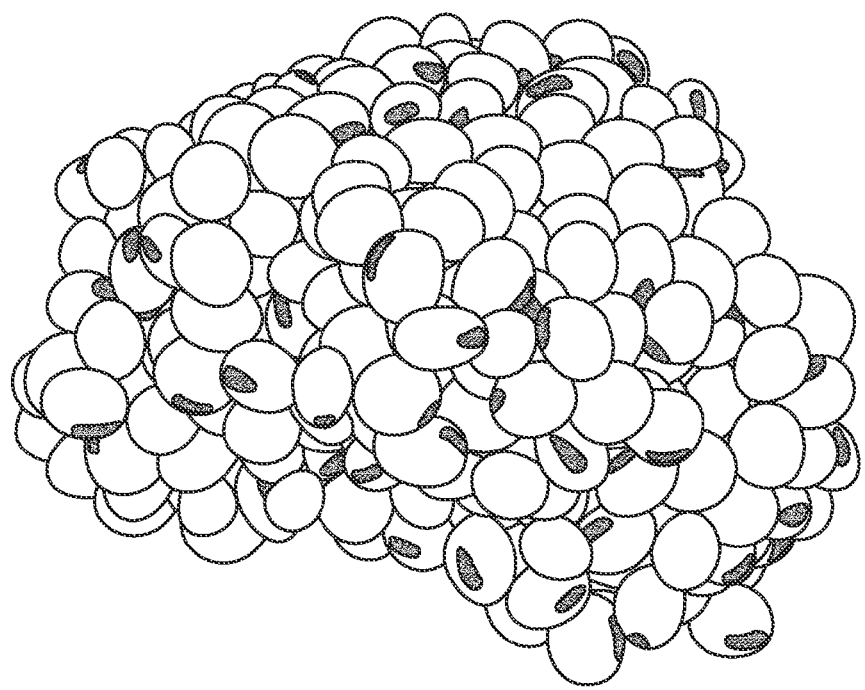
FIG. 1B depicts seed exhibiting seed bridging.

As an example, FIG. 1A depicts seed that is not exhibiting bridging. That is, the seed are not adhered to each other and thus are being retained in a dish. In contrast, FIG. 1B depicts seed that are exhibiting seed bridging. That is, the seed are adhered to each other based on a stickiness created by a seed treatment, thereby resulting in a mass or clump of seed.

The composition embodiments disclosed here can be mixed with or applied to seed in conjunction with various seed treatments and thereby reduce the seed bridging of the seed that might otherwise occur, and, in some embodiments, enhance the survivability of any beneficial microorganisms in the composition.

The various compositions contemplated herein can include any known sugar for use in seed treatment compositions containing or intended for use with beneficial microorganisms. In one embodiment, the sugar is either sucrose or sorbitol. Alternatively, the sugar can be any known non-reducing sugar. According to one implementation, the sugar is present in the composition in an amount ranging from about 30% to about 70% weight per volume ("% w/v"). Alternatively, the sugar is present in an amount ranging from about 35% to about 65% w/v. In a further alternative, the sugar is present in an amount ranging from about 40% to about 60% w/v. In yet another alternative, the sugar is present in an amount ranging from about 45% to about 55% w/v.

In accordance with one implementation, the oil is either mineral oil or silicon oil or a mixture thereof. Alternatively, the oil can be any heavy lubricating oil or a mixture thereof. According to one embodiment, the oil is present in the composition in an amount ranging from about 5% to about 60% w/v. Alternatively, the oil is present in the composition in an amount ranging from about 10% to about 55% w/v. In a further alternative, the oil is present in the composition in an amount ranging from about 20% to about 50% w/v.

The emulsifying agent, in one embodiment, is lecithin. Alternatively, the emulsifying agent can be any polysorbate emulsifying agent. In a further alternative, the emulsifying agent is any known emulsifying agent that is used in treatment compositions for seeds, seedlings, or plants. According to one implementation, the emulsifying agent is present in the composition in an amount ranging from about 0.05% to about 12% w/v. Alternatively, the emulsifying agent is present in the composition in an amount ranging from about 0.1% to about 6% w/v. Alternatively, the emulsifying agent is present in the composition in an amount ranging from about 0.15% to about 3% w/v. Alternatively, the emulsifying agent is present in the composition in an amount ranging from about 0.25% to about 1.5% w/v. According to one implementation, the emulsifying agent is present in the composition in an amount ranging from about 0.5% to about 1.0% w/v.

In certain alternative embodiments, the various composition implementations can also include a buffer component. According to one embodiment, the buffer component can be any known buffer component for use in a composition for application to seeds, seedlings, or plants.

It is understood that any of the composition embodiments contemplated herein can include, as an additional, alternative component, any commercially available extender composition. For purposes of this application, "extender" or "extender composition" includes any composition configured to increase microorganism survival or performance upon or after application to a seed, seedling, or plant. Such compositions can include, for example, conditioners and other such compositions. One example of such an extender composition is the Liquid Extender™ product available from Becker Underwood, Inc. in Ames, Iowa. In certain embodiments in which a composition embodiment as contemplated herein includes, as an additional component, a commercially available extender composition, the composition can include solely an oil, an emulsifier, and the commercially available extender composition. Alternatively, any implementations disclosed herein can be applied in conjunction with such a commercially available extender composition. That is, both compositions are applied to the seed, seedling, or plant at the same time or are mixed together before application.

According to an alternative embodiment, the composition can also include a beneficial microorganism. In one version, the microorganism is any microorganism from the *Rhizobium* or *Bradyrhizobium* genera, including, for example, *Bradyrhizobium japonicum, Rhizobium meliloti, Bradyrhizobium* spp, *Rhizobium* spp, *Sinorhizobium meliloti, R. leguminosarum* bv. viceae, *R. leguminosarum* bv. phaseoli, *R. leguminosarum* bv. trifolii, *Mesorhizobium* spp, *Azospirillum* spp, or *Azorhizobium* spp. Alternatively, the microorganism is any other bacteria used in seed treatments. In further embodiments, the microorganism is any other microorganism used in seed, seedling, or plant treatments.

Alternatively, in addition to a first beneficial microorganism, the composition can also include one or more additional beneficial microorganisms. In one implementation, the additional beneficial microorganism(s) can act as a complementary plant growth promoter in concert with the first beneficial microorganism. For example, in one embodiment, the composition can also include *Bacillus subtilis*, which can act as a complementary plant growth promoter in concert with *B. japonicum* or another of the microorganisms discussed above.

In accordance with one implementation, certain composition embodiments as disclosed or contemplated herein can enhance the survivability of any beneficial microorganism included in the composition or added to the seed with the composition. More specifically, a beneficial microorganism such as *B. japonicum* can survive longer on the seed if the *B. japonicum* is first added to a composition containing at least a sugar and an oil according to various embodiments disclosed or contemplated herein or is added to the seed along with the composition. Alternatively, certain compositions containing a sugar, an oil, and any other component disclosed herein can also enhance the survivability of a beneficial microorganism.

According to another embodiment, certain composition embodiments as contemplated herein that contain at least one beneficial microorganism or are mixed with at least one beneficial microorganism or added to the seed with at least one microorganism can further enhance the yield of the plants that grow from the seed. More specifically, the combination of a composition containing at least oil and a beneficial microorganism (such as, for example, *B. japonicum*) and application of that combination to seed can result in plants growing from the seed that exhibit greater yield than seed to which the combination has not been applied. Alternatively, certain compositions containing an oil and at least one microorganism with any combination of a sugar, an emulsifier, and/or and any other component disclosed herein can also enhance the yield of the plants growing from the seed to which the composition is applied.

In yet another alternative implementation, the composition can also include a polymer component. In one specific example, the polymer component can be polyvinylpyrrolidone or polyvinylpyrillidone vinyl acetate or a mixture thereof. Alternatively, the polymer component can be any known polymer component, or any mixture of two or more such components, used in seed, seedling, or plant treatment compositions. Some non-limiting examples of such polymers that may be natural or synthetic are biopolymers, acrylic emulsions, acrylic copolymers, styrenated acrylic polymers, styrene copolymers, butadiene-styrene copolymers, polyvinylacrylates, polyvinyl acetates, polyvinyl alcohols, polyvinyl alcohol copolymers. According to one implementation, the polymer component does not phytotoxically affect the seed.

In a further alternative embodiment, the composition can also include a pesticide. The pesticide, in accordance with one implementation, can be any commercially available pesticide that can be or is typically applied to seed as a seed treatment product. In one specific example, the pesticide can be CruiserMaxx®, which is commercially available from Syngenta, which is located in Switzerland. Alternatively, any known seed treatment pesticide product can be used.

In accordance with one implementation, certain composition embodiments as contemplated herein that contain a pesticide can further enhance the survivability of any beneficial microorganism included in the composition or added to the seed with the composition. More specifically, a beneficial microorganism such as *B. japonicum* can survive longer on the seed if the *B. japonicum* is first added to a composition containing at least a sugar, an oil, and a pesticide according to various embodiments disclosed or contemplated herein or is added to the seed along with the composition. Alternatively, certain compositions containing a sugar, an oil, a pesticide, and any other component disclosed herein can also enhance the survivability of a beneficial microorganism.

In use, any of the various compositions herein can be applied to seed (such as, for example, soybean seed) prior to planting. In one embodiment, the various components of the composition are mixed together and then applied to the seed. Alternatively, certain components—such as, for example, the oil and sugar—are mixed together first and then applied to the seed at the same time as other components (such as, for example, a pesticide, a beneficial microorganism, etc.).

According to one implementation, a composition containing mineral oil, sugar, an emulsifier, and an extender can be applied to seed at a rate ranging from about 0.15 fluid ounces per 100 pounds of seed to about 1.5 fluid ounces per 100 pounds of seed. Alternatively, that composition can be applied at a rate of from about 0.3 fl. oz./100 lbs to about 1.3 fl. oz./100 lbs. In a further alternative, the composition is applied at a rate of from about 0.45 fl. oz./100 lbs to about 1.0 fl. oz./100 lbs. In yet another alternative, the rate can be from about 0.6 fl. oz./100 lbs. to about 0.8 fl. oz./100 lbs. According to another alternative implementation, the rate is about 0.74 fl. oz./100 lbs. Another alternative relates to a rate of about 0.86 fl. oz./100 lbs.

EXAMPLES

Example 1

On-Seed Survival of *B. Japonicum* in Compositions Containing Oils

In this example, the survivability of *B. japonicum* was examined in compositions containing varying amounts of certain oils.

The seed treatment composition was a liquid composition containing two strains of *B. japonicum*, obtained from the Vault® HP product, which is commercially available from Becker Underwood, Inc. of Ames, Iowa. The composition also contained sucrose (60% w/v), dipotassium phosphate (1% w/v), and lecithin (1% w/v). The lecithin is commercially available as Emulfluid E™ from Cargill in Minnesota. In addition, the various compositions contained varying amounts of certain oils, as shown in Table 1 below.

TABLE 1

| Test Composition | Oil | % Oil w/v |
|---|---|---|
| 1 | Control | 0 |
| 2 | Mineral oil | 5 |
| 3 | Mineral oil | 10 |
| 4 | Mineral oil | 50 |
| 5 | Silicone oil | 5 |
| 6 | Silicone oil | 10 |
| 7 | Silicone oil | 50 |
| 8 | Sunflower oil | 5 |
| 9 | Sunflower oil | 10 |
| 10 | Sunflower oil | 50 |

The mineral oil used in test compositions 2, 3, and 4 was a mineral oil obtained from Sigma Aldrich, located in St. Louis, Mo. (the product was Catalog #33076 in the Sigma Aldrich catalog). The silicone oil used in test compositions 5, 6, and 7 was a silicone oil product called Silicone fluid DC 200/300 which is available from Ellis and Everard, located in England. The sunflower oil used in test compositions 8, 9, and 10 was a sunflower oil product available from Silbury Marketing, located in England.

For each composition, 100 ml of the composition was prepared by mixing together the sucrose and the oil component. With respect to test compositions 2, 3, and 4, the mineral oil was added to the sucrose and the resulting composition was emulsified using an MR550 HC handheld blender, which is commercially available from Braun, located in Germany.

For each test composition, once the sucrose, dipotassium phosphate, lecithin, and oil components were mixed together, the resulting mixture was then mixed with the *Rhizobium* broth at a volumetric ratio of 1:1. The resulting mixture was then applied to soybean seeds at a rate of 2.8 ml/kg seed. The application to the seeds was accomplished by mixing 500 grams of seed with 1.4 ml of the mixture in a Ziploc™ bag and mixing the contents until the mixture coated the seeds evenly. The resulting treated seeds were then incubated at 18° C. with the bag vented.

To assess the survivability of the *Rhizobium*, the seeds were periodically sampled and each such sample was assessed for the number of viable rhizobia/seed. The resulting *rhizobium* numbers over time are presented in FIG. 1.

The survivability assessment results show that a composition containing either silicone oil or mineral oil at various concentrations had no adverse impact on rhizobial survival in comparison to the control composition (composition 1, which contained no oil). In contrast, the compositions containing sunflower oil at various concentrations resulted in less *rhizobium* on the seeds in comparison to the control composition. Hence, it appears that compositions containing either mineral oil or silicone oil are preferred over compositions containing sunflower oil to enhance or maintain *Rhizobium* viability.

Example 2

On-Seed Survival of *B. japonicum* in Compositions Containing Oils Along with a Commercial Extender and Pesticide Treatment In this example, the survivability of *B. japonicum* was examined in compositions containing mineral oil, an emulsifying agent, a commercially available extender, and/or one of two commercially available pesticide treatments.

The liquid compositions contained *B. japonicum*, obtained from the Nodulator® N/P product, which is commercially available from Becker Underwood, Inc. of Ames, Iowa. Some of the compositions also contained at least one liquid extender product called Liquid Extender™, which is commercially available from Becker Underwood, Inc. in Ames, Iowa (and contains sugar), CruiserMaxx® (the pesticide seed treatment product discussed above), Apron Maxx® RFC (a pesticide seed treatment product available from Syngenta Crop Protection and/or beneficial microorganism *Bacillus subtilis*, which can act as a complementary plant growth promoter in concert with the *B. japonicum*. More specifically, each of the four test compositions contained a different mixture of components as set forth in Table 2 below. The oil composition as listed in Table 2 is made up of a mixture of the mineral oil used in Example 1 and 2% w/v of lecithin, which is mixed with Liquid Extender™ such that the ratio of the components is 20% of the mineral oil and lecithin to 80% Liquid Extender™. The amounts of each component are provided in milliliters of the component per kilogram of seed.

TABLE 2

| Composition | Rhizobium (ml/kg) | Oil Composition (ml/kg) | Liquid Extender ™ (ml/kg) | CruiserMaxx ® (ml/kg) | Apron Maxx ® RFC (ml/kg) | Bacillus subtilis (ml/kg) |
|---|---|---|---|---|---|---|
| 1 | 2.7 |      | 0.48 |      |      | 0.1 |
| 2 | 2.7 | 0.48 |      |      |      | 0.1 |
| 3 | 2.7 |      | 0.48 | 1.95 |      | 0.1 |
| 4 | 2.7 | 0.48 |      | 1.95 |      | 0.1 |
| 5 | 2.7 |      | 0.48 |      | 0.98 | 0.1 |
| 6 | 2.7 | 0.48 |      |      | 0.98 | 0.1 |

Figure 2:
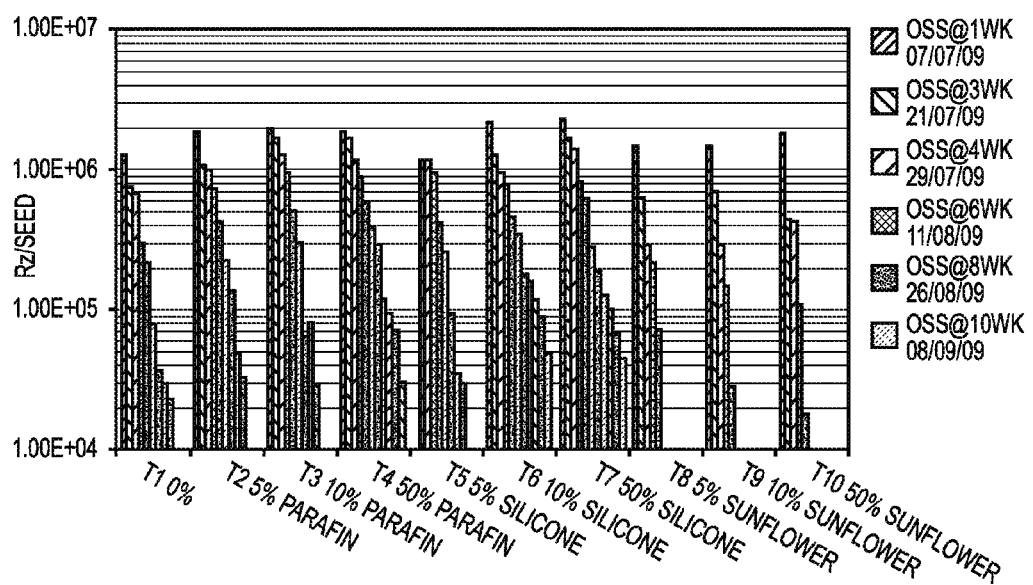
FIG. 2 is a bar graph showing the on-seed survival of *B. japonicum* in various compositions over time, according to one embodiment.

The survivability assessment (on-seed survival) results are shown in table form below in Table 3 and in graphical form in FIG. 2.

TABLE 3

| Time | Compositions | | | | | |
|---|---|---|---|---|---|---|
| | 1 | 2 | 3 | 4 | 5 | 6 |
| 0 wk | 9.60E+05 | 1.20E+06 | 1.30E+06 | 1.10E+06 | 1.70E+06 | 2.00E+06 |
| 1 wk | 3.20E+05 | 4.80E+05 | 4.60E+05 | 5.80E+05 | 6.80E+05 | 7.40E+05 |
| 2 wks | 2.60E+05 | 3.40E+05 | 4.00E+05 | 4.20E+05 | 5.20E+05 | 5.20E+05 |
| 3 wks | 1.50E+05 | 2.40E+05 | 2.00E+05 | 3.00E+05 | 3.00E+05 | 2.60E+05 |
| 4 wks | 1.50E+05 | 2.00E+05 | 2.20E+05 | 3.80E+05 | 2.80E+05 | 3.00E+05 |
| 5 wks | 1.40E+05 | 1.70E+05 | 1.80E+05 | 2.60E+05 | 2.20E+05 | 2.00E+05 |
| 6 wks | 8.20E+04 | 1.10E+05 | 1.50E+05 | 1.80E+05 | 2.20E+05 | 2.20E+05 |
| 7 wks | 6.80E+04 | 1.20E+05 | 1.40E+05 | 1.70E+05 | 1.70E+05 | 1.30E+05 |
| 8 wks | 3.40E+04 | 5.20E+04 | 5.60E+04 | 1.00E+05 | 6.20E+04 | 1.10E+05 |
| 9 wks | 3.80E+04 | 6.00E+04 | 8.00E+04 | 1.10E+05 | 9.40E+04 | 1.20E+05 |

These results show not only that a composition containing mineral oil with or without the CruiserMax® or Apron Maxx® RFC pesticide components had no adverse impact on rhizobial survival in comparison to the control composition, but also that these compositions can enhance rhizobial survival in comparison to the control. More specifically, as set forth in Table 3, compositions 2, 4, and 6 generally exhibit longer on-seed survival (calculated as number of rhizobia per seed) over the same period of time in comparison to the respective control compositions. That is, application of composition 2 to seed results in the rhizobia included with composition 2 surviving longer than the rhizobia in composition 1 over the same period of time, while composition 4 results in the rhizobia surviving longer than those in composition 3, and the rhizobia in composition 6 also survived longer than those in composition 5. In fact, it can also be noted that combination of a pesticide and the oil composition enhances on-seed survival to a greater extent than either the oil composition or the pesticide alone, especially during the later time periods such as 5, 7, or 9 weeks. As such, in addition to enhancing on-seed survival on its own, the oil composition also enhances the effect of the pesticide.

Example 3

Examination of Bridging Reduction

In this example, the ability of a composition containing mineral oil to reduce bridging of seeds to which the composition is applied.

Two lots of seeds—each lot weighing 15,000 lbs.—were treated using a seed treater called an LP2000, which is commercially available from USC, located in Kansas. As set forth in Table 4, one lot was treated with Composition 1, and the other lot was treated with Composition 2. Generally, Composition 1 included a standard commercial extender, while Composition 2 included the commercial extender along with mineral oil. More specifically, the Oil Composition in Composition 2 was mixed in the same way with the same components as the Oil Composition described in Example 2. The various components were mixed into a fine emulsion using a BraunMR550 HC handheld blender.

TABLE 4

| | | | Compositions (ml/kg seed) | |
|---|---|---|---|---|
| | Component | Supplier | Composition 1 | Composition 2 |
| Rhizobium inoculant | Nodulator® N/T liquid | Becker Underwood | 2.7 | 2.7 |
| Bacillus subtilis inoculant | rhizobium Integral ™ | Becker Underwood | 0.1 | 0.1 |
| Extender | Liquid Extender ™ | Becker Underwood | 0.48 | |
| Oil Composition | 80% Liquid Extender ™ with 20% mineral oil and emulsifying agent | Becker Underwood And Sigma Aldrich | | 0.48 |
| Insecticide & Fungicide | CruiserMaxx ® Beans | Syngenta Crop Protection | 1.95 | 1.95 |

Figure 3:
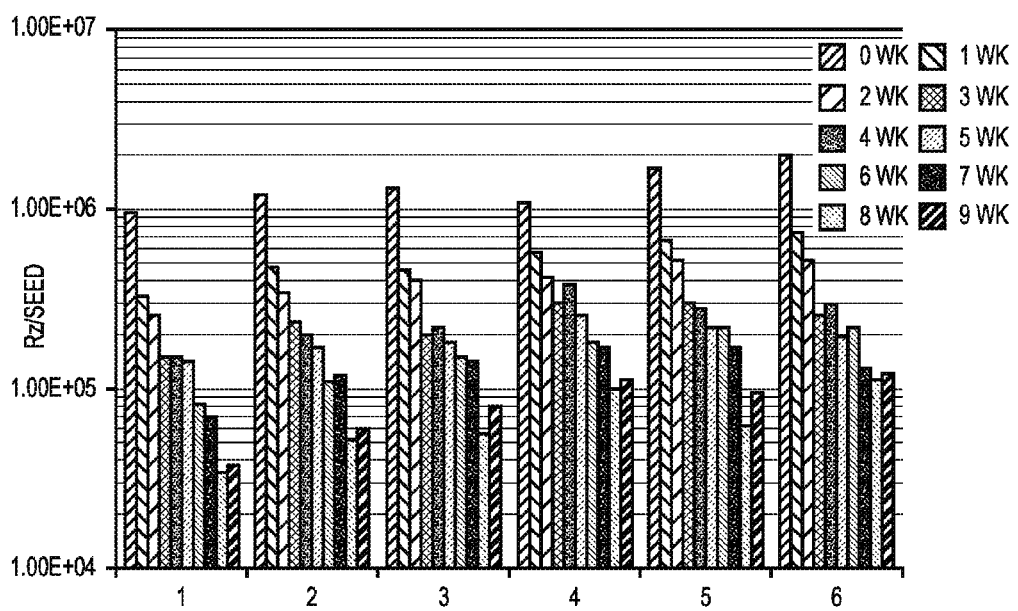
FIG. 3 is a bar graph showing the on-seed survival of *B. japonicum* in various compositions over time, according to one embodiment.
Figure 4:
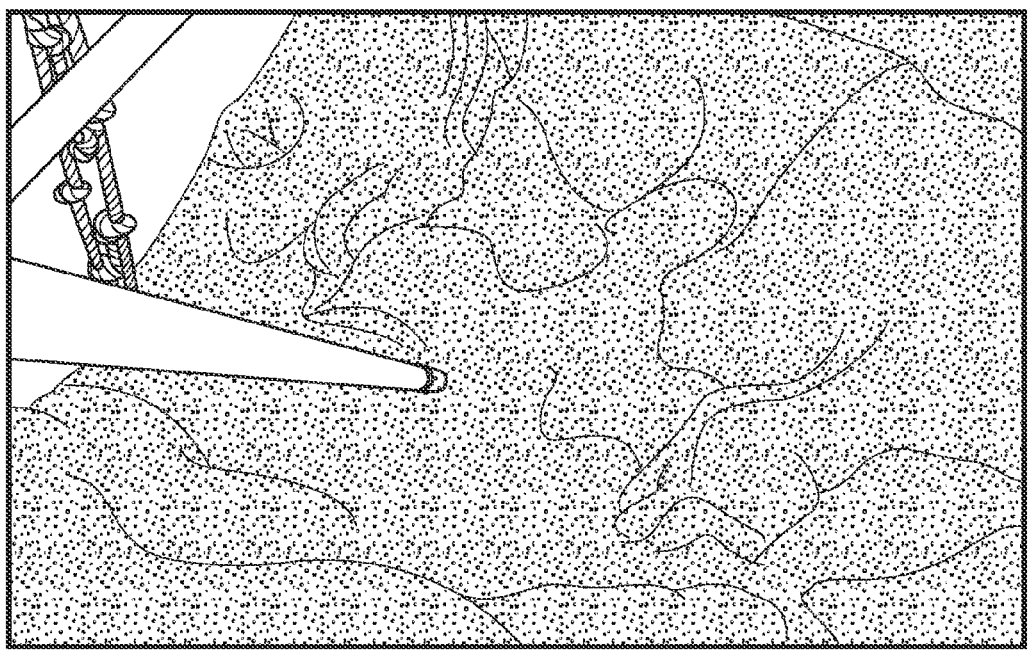
FIG. 4 depicts seed bridging of seeds treated with a standard commercial extender.

The comparative bridging results for soybeans treated with the compositions are shown in FIGS. 3 and 4. More specifically, the bridging results for soybeans treated with Composition 1 are shown in FIG. 3 and the results for soybeans treated with Composition 2 are shown in FIG. 4. The seeds treated with Composition 1 adhered to each other to such an extent that the seeds adhered to each other in a large mass and could not flow from the hopper without significant mechanical assistance, and the resulting bridging is depicted in FIG. 3. In contrast, the adhesion of the seeds treated with Composition 2 was reduced to the point that the seeds did not experience bridging and thus were able to flow without mechanical assistance, as shown in FIG. 4.

Example 4

On-Seed Survival of Rhizobia in Composition Embodiment Combined with Various Pesticides In this example, the survivability of B. japonicum was examined in a mineral oil composition in combination with one of six commercially-available pesticide treatments, as set forth in detail below. More specifically, the on-seed survival of the B. japonicum was examined. As used herein, "on-seed survival" means ability of microorganisms to remain viable after application to seed, often as a component of a seed treatment.

The test composition contained the ingredients set forth in Table 5, including an oil, an emulsifier, and a sugar. In this particular composition, the sugar was a component of the Liquid Extender™. The oil and emulsifier was mixed with the Liquid Extender™ such that the oil made up 20% of the mixture, the emulsifier made up 2% of the mixture, and the Liquid Extender™ made up 78% of the mixture. In this example, the oil was white mineral oil, available from Calumet Lubricants Co. in Indianapolis, Ind., and the emulsifier was soy lecithin, available from Columbus Foods Company, Inc. in Des Plaines, Ill. As set forth in Table 6, the control composition contained the commercially-available ingredients of Vault HP, which is commercially available from Becker Underwood, Inc. in Ames, Iowa. More specifically, the control composition contained all of the same components as the test composition except for the oil.

TABLE 5

| Test Composition Components | Amount (fl. oz./cwt) | Amount (ml/100 lb) |
|---|---|---|
| B. japonicum | 1.0 | 29.57 |
| Liquid Extender ™ + Oil + Emulsifier | 0.87 | 25.7 |
| Integral ® | 0.14 | 4.14 |
| Total | 2.01 | 59.14 |

TABLE 6

| Control Components | Amount (fl. oz./cwt) | Amount (ml/100 lb) |
|---|---|---|
| B. japonicum | 1.0 | 29.57 |
| Liquid Extender ™ | 0.87 | 25.7 |
| Integral ® | 0.14 | 4.14 |
| Total | 2.01 | 59.14 |

Six different pesticides were tested for on-seed survival in combination with the test and control compositions described above. The composition of each pesticide is set forth in below. The Acceleron™ pesticide package is set forth in Table 7. The Trilex 6000™ pesticide package is set forth in Table 8. The pesticide preparation of Cruisser Maxx combined with Avicta is set forth in Table 9. The Cruisser Maxx PLUS pesticide package is set forth in Table 10. The pesticide preparation of Cruisser Maxx PLUS combined with Avicta is set forth in Table 11. The pesticide preparation of Rancona combined with Metastar is set forth in Table 12.

TABLE 7

| Component | Amount (fl. oz./cwt) | Amount (ml/100 lb) |
|---|---|---|
| F500 | 0.40 | 11.83 |
| Allegiance FL | 0.80 | 23.65 |
| Gaucho 600 | 1.60 | 47.30 |
| N-Hibit Gold CST | 0.25 | 7.39 |
| CCR | 0.80 | 23.65 |
| Seed Gloss | 0.40 | 11.83 |
| Total | 4.25 | 125.6 |

TABLE 8

| Component | Amount (fl. oz./cwt) | Amount (ml/100 lb) |
|---|---|---|
| Water | 1.39 | 41.10 |
| Pro-Ized Red Colorant | 0.5 | 14.78 |

TABLE 8-continued

| Component | Amount (fl. oz./cwt) | Amount (ml/100 lb) |
|---|---|---|
| Yield shield | 0.5 | 14.78 |
| Trilex 2000 | 1.0 | 29.57 |
| Gaucho 600 | 1.6 | 47.30 |
| Precise soybean | 1.0 | 29.57 |
| Total | 5.99 | 177.10 |

TABLE 9

| Component | Amount (fl. oz./cwt) | Amount (ml/100 lb) |
|---|---|---|
| Cruisser Maxx | 2.95 | 87.3 |
| Avicta 500 | 3.0 | 88.8 |
| Total | 5.95 | 176.1 |

TABLE 10

| Component | Amount (fl. oz./cwt) | Amount (ml/100 lb) |
|---|---|---|
| Cruisser Maxx PLUS | 3.21 | 95 |
| Water | 0 | 0 |
| Total | 3.21 | 95 |

TABLE 11

| Component | Amount (fl. oz./cwt) | Amount (ml/100 lb) |
|---|---|---|
| Cruisser Maxx PLUS | 3.21 | 95 |
| Avicta 500 | 3.0 | 88.8 |
| Total | 6.21 | 183.8 |

TABLE 12

| Component | Amount (fl. oz./cwt) | Amount (ml/100 lb) |
|---|---|---|
| Rancona 3.8FS | 0.085 | 2.51 |
| Metastar | 0.75 | 22.17 |
| Water | 2.16 | 63.94 |
| Total | 2.995 | 88.65 |

Figure 5:
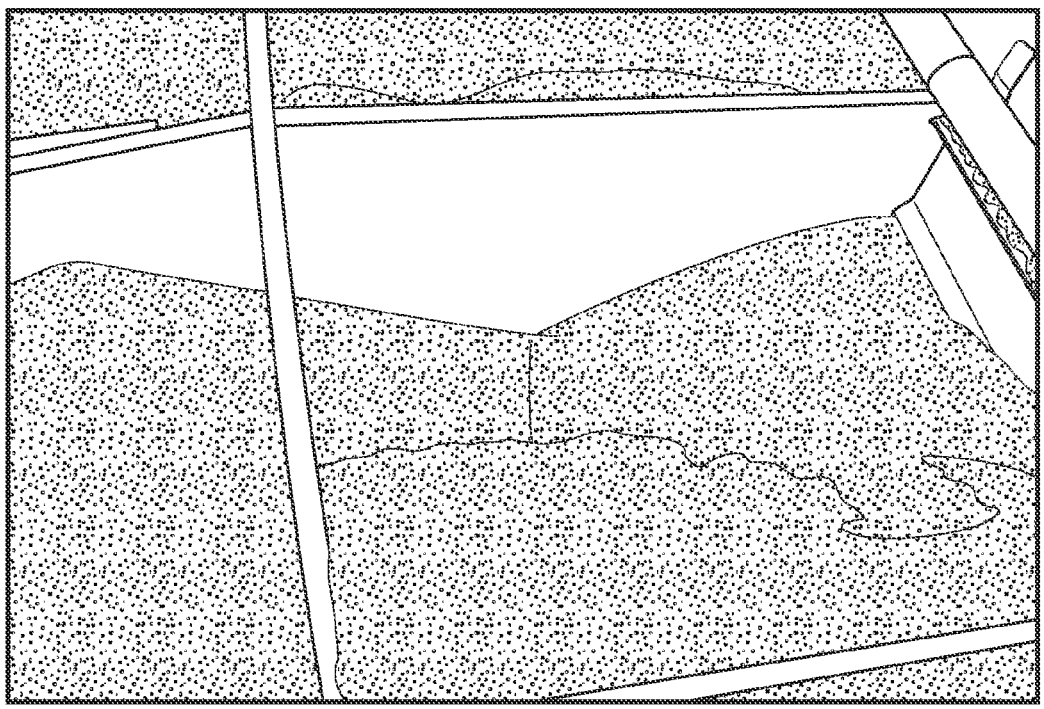
FIG. 5 depicts the lack of much seed bridging, if any, of seeds treated with a composition containing mineral oil, according to one embodiment.

The on-seed survival results are shown in graphical form in FIG. 5. As shown, the compositions were examined to identify the number of days after the treatment that were more than $1 \times 10^5$ rhizobia per seed. These results show not only that a composition containing mineral oil with or without the CruiserMax® or Apron Maxx® RFC pesticide components had no adverse impact on rhizobial survival in comparison to the control composition, but also that these compositions can enhance rhizobial on-seed survival in comparison to the control. More specifically, as set forth in Table 3, compositions 2, 4, and 6 generally exhibit greater on-seed survival (calculated as number of days after treatment during which there are greater than $1 \times 10^5$ rhizobia per seed) in comparison to the respective control compositions. That is, application of composition 2 to seed results in more of the rhizobia surviving longer than the rhizobia in composition 1 over the same period of time, while composition 4 results in more of the rhizobia surviving longer than those in composition 3, and more of the rhizobia in composition 6 also survived longer than those in composition 5. In fact, it can also be noted that combination of a pesticide and the oil composition enhances on-seed survival to a greater extent than either the oil composition or the pesticide alone, especially during the later time periods such as 5, 7, or 9 weeks. As such, in addition to enhancing on-seed survival on its own, the oil composition also enhances the effect of the pesticide.

Example 5

Impact on Soybean Yields of Oil Composition Applied with Rhizobia

In this example, the impact of an oil composition on soybean yields was assessed. More specifically, certain compositions containing rhizobia were applied to soybeans and the resulting yields of those soybeans were examined.

The four compositions contained the ingredients set forth in Table 13. As shown, each composition contained rhizobia, with compositions 1 and 2 containing rhizobia obtained from the Vault® HP product described above in Example 2 and compositions 3 and 4 containing rhizobia obtained from the Vault® NP product, also sold by Becker Underwood, Inc. All four compositions also contained the Liquid Extender™ product described above in Example 2, with compositions 2 and 4 containing a mixture of Liquid Extender™, mineral oil, and emulsifier such that the relative amount of the components is 20% mineral oil, 2% emulsifier, and 78% Liquid Extender™. As with Example 5, the sugar was a component of the Liquid Extender™, the oil was white mineral oil, available from Calumet Lubricants Co. in Indianapolis, Ind., and the emulsifier was soy lecithin, available from Columbus Foods Company, Inc. in Des Plaines, Ill.

TABLE 13

| Composition | Vault® HP Rhizobia (ml/kg) | Vault® NP Rhizobia (ml/kg) | Liquid Extender™ (ml/kg) | Liquid Extender™ with Oil & Emulsifier (ml/kg) | Chlorine Free Water |
|---|---|---|---|---|---|
| 1 | 0.65 | | 0.6 | | 2.05 |
| 2 | 0.65 | | | 0.6 | 2.05 |
| 3 | | 2.74 | 0.5 | | |
| 4 | | 2.74 | | 0.5 | |

Figure 6:
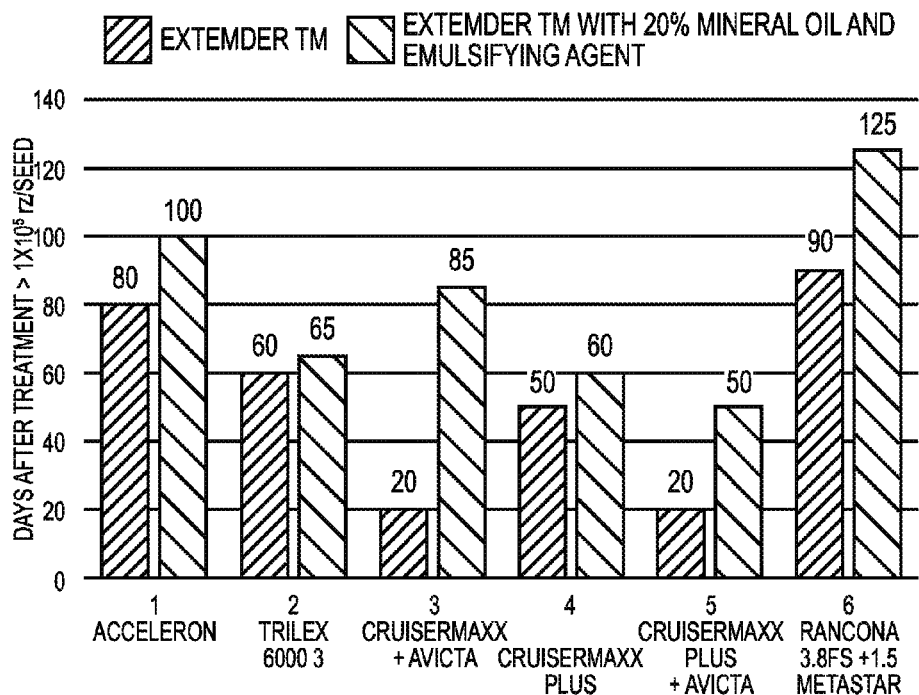
FIG. 6 is a bar graph showing the on-seed survival of *B. japonicum* in various compositions combined with various pesticides over time, according to one embodiment.
Figure 7:
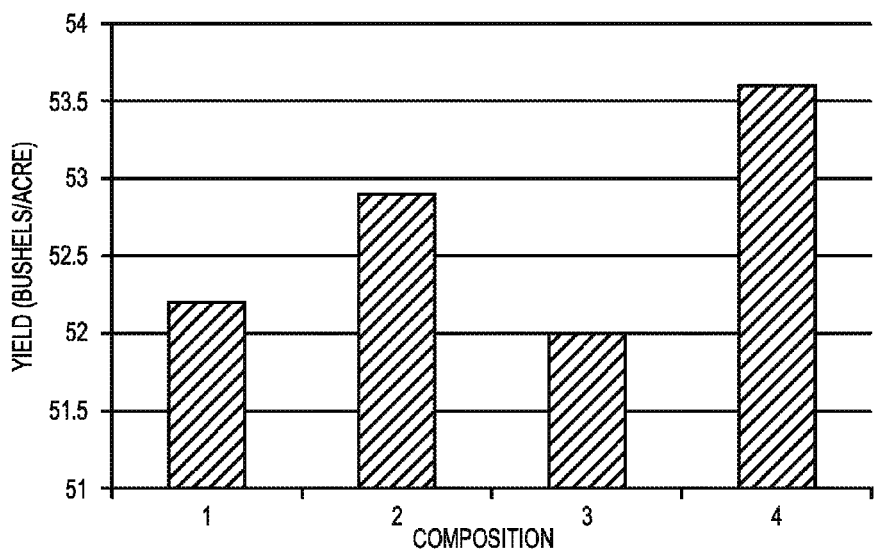
FIG. 7 is a bar graph showing the yield of plants resulting from seeds treated with various compositions, according to one embodiment.

Seeds were treated with the compositions set forth in Table 13. More specifically, each of four groups of seed were treated with one of the compositions, planted, and harvested. Seven field trials were carried out at different locations and the mean harvest yield of the soybeans was determined. The results are set forth in Table 14 below and graphically in FIG. 6. As shown in the table and the figure, the combination of the mineral oil with the Liquid Extender™ showed a mean improvement in yields over the Liquid Extender™ alone for both the Vault® HP and the Vault® NP rhizobial compositions, with increases of 0.7 and 1.6 bushels/acre, respectively. As such, these results show that a composition containing mineral oil in addition to rhizobia can enhance soybean yield in comparison to the control.

Although the present invention has been described with reference to preferred embodiments, persons skilled in the art will recognize that changes may be made in form and detail without departing from the spirit and scope of the invention.

What is claimed is:

1. A liquid seed treatment composition comprising:
   (a) a first seed treatment component, comprising:
      i. at least one non-reducing sugar present in an amount ranging from about 30% to about 70% w/v, wherein the at least one non-reducing sugar is selected from the group consisting of sucrose and sorbitol;
      ii. at least one oil present in an amount ranging from about 5% to about 60%, wherein the at least one oil is selected from the group consisting of mineral oil and silicon oil;
      iii. an emulsifying agent present in an amount of about 0.15 to about 3% w/v, wherein the emulsifying agent is selected from the group consisting of lecithin and polysorbate; and
   (b) a second seed treatment component further comprising at least one non-dormant microorganism, wherein the second seed treatment component is added to the first seed treatment component; wherein the presence of said oil reduces seed bridging as well as improves the survivability of the non-dormant microorganism.

2. The liquid seed treatment composition of claim 1, further comprising a pesticide.

3. The composition of claim 1, wherein the composition is effective in enhancing yield of plants growing from seeds.

4. A liquid seed treatment composition comprising:
   (a) a non-reducing sugar present in the amount of about 30% to about 70% w/v, wherein the non-reducing sugar comprises sucrose or sorbitol;
   (b) an oil present in the amount of about 5% to about 60% w/v, wherein the oil comprises at least one of mineral oil or silicon oil;
   (c) lecithin, wherein the non-reducing sugar component, the oil component and lecithin are combined as a treatment component; and
   (d) at least one non-dormant microorganism, wherein the non-dormant microorganism is then added to the treatment component; wherein the presence of said oil reduces seed bridging as well as improves the survivability of the non-dormant microorganism.

5. The composition of claim 4, wherein the lecithin is present in an amount ranging from about 0.05% to about 6.0% w/v.

6. The composition of claim 4, wherein the at least one microorganism is *Rhizobium*.

7. The composition of claim 4, wherein the composition enhances the survivability of the at least one microorganism.

8. The composition of claim 4, wherein the composition is effective in enhancing yield of plants growing from seeds.

9. A liquid seed treatment composition comprising:
   (a) a seed treatment mixture comprising:
      i. at least one non-reducing sugar present in an amount ranging from about 30% to about 70% w/v, wherein the at least one non-reducing sugar is selected from the group consisting of sucrose and sorbitol;
      ii. at least one heavy lubricating oil present in an amount ranging from about 5% to about 60% w/v, wherein the at least one heavy lubricating oil is selected from the group consisting of mineral oil and silicon oil;
      iii. an emulsifying agent present in an amount of about 0.15% to about 3.0% w/v; wherein the emulsifying agent is selected from the group consisting of lecithin and polysorbateand
   (b) at least one non-dormant microorganism, wherein the at least one non-dormant microorganism is added to the seed treatment mixture; wherein the presence of said oil reduces seed bridging as well as improves the survivability of the non-dormant microorganism.

10. The seed treatment of claim 9, further comprising at least one polymer component.

11. The seed treatment of claim 9, further comprising a commercial extender composition.

12. The seed treatment of claim 9, further comprising a commercial extender composition, wherein the at least one non-reducing sugar is a component of the commercial extender composition.

13. The seed treatment of claim 9, further comprising a buffer component.

14. The seed treatment of claim 9, further comprising a pesticide.

15. The seed treatment of claim 9, wherein the at least one microorganism is a *Rhizobium*.

16. The seed treatment of claim 9, further comprising a mixture of at least two microorganisms.

* * * * *